Figure 1:
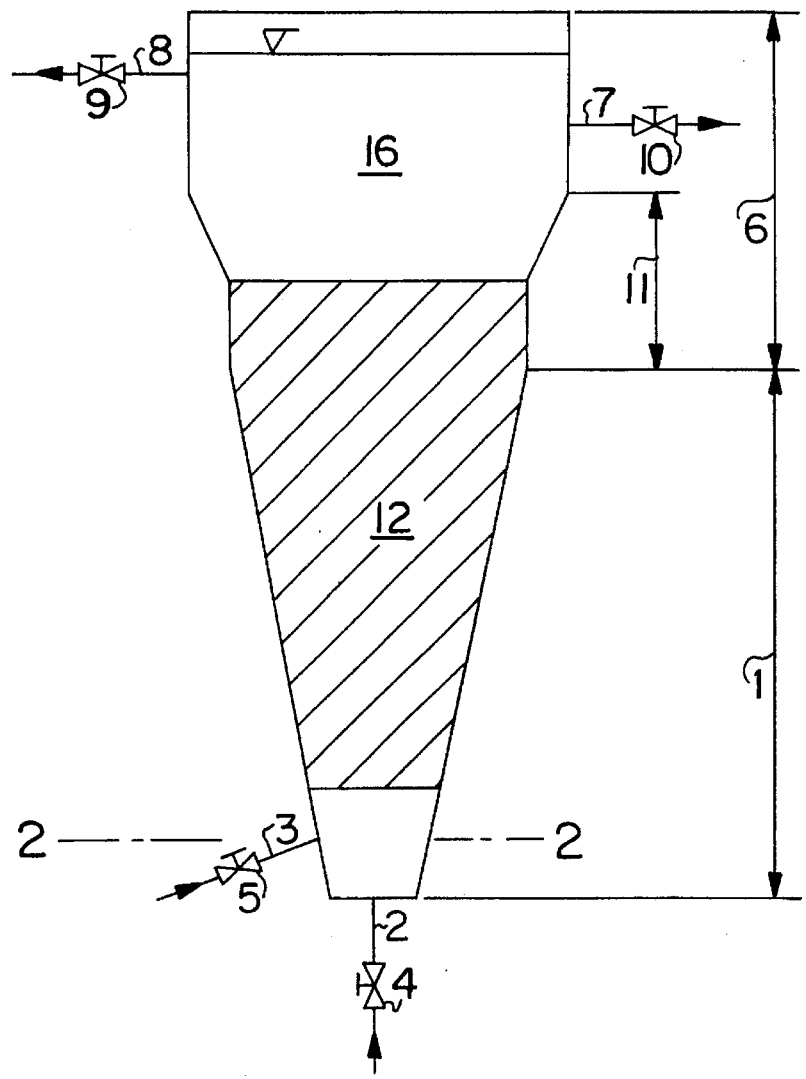

United States Patent [19]

Donner et al.

[11] Patent Number: 5,618,411

[45] Date of Patent: Apr. 8, 1997

[54] FLUIDIZED-BED FERMENTER

[75] Inventors: Christoph Donner, Kleinmachnow; Stephan Sokolowsky; Lothar Reinke, both of Berlin, all of Germany

[73] Assignee: Schering Aktiengesellschaft, Berlin, Germany

[21] Appl. No.: 331,635

[22] PCT Filed: May 5, 1993

[86] PCT No.: PCT/DE93/00414

§ 371 Date: Feb. 3, 1995

§ 102(e) Date: Feb. 3, 1995

[87] PCT Pub. No.: WO93/22246

PCT Pub. Date: Nov. 11, 1993

[30] Foreign Application Priority Data

May 7, 1992 [DE] Germany ............... 42 14 896.0

[51] Int. Cl.⁶ ....................................... C02F 3/08
[52] U.S. Cl. .............................. 210/150; 210/617
[58] Field of Search ........................ 210/150, 151, 210/617, 618, 220

[56] References Cited

U.S. PATENT DOCUMENTS

| | | | |
|---|---|---|---|
| 3,232,434 | 2/1966 | Albertsmeyer | 210/617 |
| 4,043,936 | 8/1977 | Francis et al. | 210/617 |
| 4,461,708 | 7/1984 | Hakulinen et al. | 210/150 |
| 4,582,600 | 4/1986 | Atkinson et al. | 210/151 |
| 4,620,931 | 11/1986 | Hirata et al. | 210/150 |
| 4,743,376 | 5/1988 | Elmaleh et al. | 210/617 |
| 4,869,815 | 9/1989 | Bernard et al. | 210/151 |

FOREIGN PATENT DOCUMENTS

| | | |
|---|---|---|
| 900159 | 5/1984 | Belgium . |
| 433139 | 6/1991 | European Pat. Off. . |
| 2102216 | 4/1972 | France . |
| 4011649 | 2/1991 | Germany . |

*Primary Examiner*—Christopher Upton
*Attorney, Agent, or Firm*—Millen, White, Zelano, & Branigan, P.C.

[57] ABSTRACT

A fluidized-bed fermenter is described, which is characterized by an inverted cone-shaped fermentation space (1) with two feed pipes (2 and 3) optionally provided with control valves (4 and 5), of which one (2) is vertically aligned to the cone vertex and the second (3) is nonvertically aligned to the shell of the cone in 0.1 to 0.3 times the height of the fermentation space and a sedimentation space (6) above fermentation space (1), which has one or two drainpipes (7 and 8) optionally provided with control valves (9 and 10).

11 Claims, 3 Drawing Sheets

FLUIDIZED-BED FERMENTER

The invention relates to a fluidized-bed fermenter, which is characterized by an inverted cone-shaped fermentation space (1) with two feed pipes (2 and 3) optionally provided with control valves (4 and 5), of which one (2) is placed vertically aligned to the cone vertex and the second (3) is nonvertically aligned to the shell of the cone in 0.02 to 0.3 times the height of the fermentation space and a sedimentation space (6) above fermentation space (1), which has one or two drainpipes (7 and 8) optionally provided with control valves, (9 and 10).

The special design of the fluidized-bed fermenter according to the invention results in that a turbulent flow prevails in its fermentation space (1), if the liquid to be fermented is fed simultaneously by vertical and horizontal feed pipes (2 and 3). This flow then merges in sedimentation space (6) in a quasi-laminar flow. If such a continuously-fed fermenter is inoculated with a microorganism culture, the latter forms pelletlike agglomerates after a growth phase because of the turbulent flow, agglomerates which are suspended in the fluidized bed of fermentation space (1) and sink again in sedimentation space (6). Because of these circumstances, the fluidized-bed fermenter according to the invention is substantially better suited for continuous fermentation of large amounts of liquid over a long period than is the case in previously known fluidized-bed fermenters, such as, for example, the device described in European Patent Specification EP-B-0258611. Consequently, the fluidized-bed fermenter according to the invention is especially suitable, for example, for biological waste-water or ground-water treatment.

The design of the fluidized-bed fermenter according to the invention is determined essentially by the type of microorganism cultures, which are to be used in it. If these are microorganism cultures which sediment relatively quickly, such as, for example, microorganism-immobilizates, as they are described in International Patent Application WO 88/08825, or fungi cultures, fluidized-bed fermenters with a fermentation space (1) and sedimentation space (6) of relatively small height are preferably used. In relatively poorly sedimenting microorganism cultures, as bacteria cultures generally are, fluidized-bed fermenters with relatively large fermentation space (1) and sedimentation space (6) are preferred. But it is not necessary that for every microorganism culture used, a specially configured fermenter be used; a continuous fermentation generally can also be achieved in fluidized-bed fermenters according to the invention not optimally configured for the special case by a corresponding adjustment of the intake rates of the liquids to be fermented by vertical and nonvertical feed pipes (2 and 3).

Generally, the fluidized-bed fermenter according to the invention is to be configured so that the upper diameter of fermentation space (1) is 0.1 to 0.8 times as large as its height. These numerical values do not take into consideration that the fermentation space normally has a truncated cone frustum, which is suitable for the reason alone that the fermenter can be more easily cleaned.

It has already been mentioned that nonvertically-aligned feed pipe (3) is arranged in the shell of the cone in 0.02 to 0.3—especially 0.05 to 0.15—times the height of fermentation space, in which two feed pipes are aligned so that in putting the fermenter in operation, a fluidized bed is produced in the fermentation space. Nonvertically-aligned feed pipe (3) can be arranged horizontally, so that the straight horizontal line pointing from the intake opening of this pipe to the axis of the fermentation space crosses this axis. But to produce a readily reproducible turbulent flow, it is suitable that the longitudinal axis of the nonvertically-aligned pipe and the straight horizontal lines pointing from the intake opening of this pipe to the axis of the fermentation space form an angle in the vertical line and/or the horizontal line, which does not exceed the value of 70° in the vertical line and the value of 60° in the horizontal line. If this feed pipe (3) is arranged directed vertically upward, the angle is preferably 10° to 60° (especially 30° to 40°), if the pipe is vertical but arranged directed downward, the angle suitably has a value between 10° and 60° (especially 20° to 45°). If feed pipe (3) optionally in addition is arranged horizontally offset, the angle is preferably 5° to 60° and especially 20° to 45°.

It is obvious to one skilled in the art that the terms "horizontal" and "vertical" are not to be understood in the mathematical sense, but that the feed pipes can deviate within the usual tolerances from an exact horizontal or vertical arrangement. Generally, feed pipes (2 and 3) are provided with usual control valves (4 and 5) and are connected by a common pipe with a storage vessel intended to accommodate the solution to be fermented.

It has already been mentioned that the fluidized-bed fermenter according to the invention has a sedimentation space (6) above fermentation space (1), which has one or preferably two drainpipes (7 and 8) optionally provided with control valves (9 and 10).

This sedimentation space (6) can be configured so that it represents a continuation without a transition of the cone-shaped fermentation space; on the other hand, it can also be configured, for example, so that it consists of one or two cylindrical components optionally provided with a conical enlargement. In this case, it can be dimensioned so that its upper diameter is 1 to 3 times (especially 1.5 to 2.5 times) the upper diameter of fermentation space (1). Sedimentation space (6) is preferably dimensioned so that it has 0.2 to 0.5 times the height of fermentation space (1). Sedimentation space (6) has one or preferably two drainpipes optionally provided with control valves (9 and 10). Two drainpipes are suitable, if it is intended to return a part of the fermented liquid to the fermentation cycle to dilute the liquid to be fermented to the extent that a practically complete conversion of the substrates contained in it can be achieved. In this case, the drainpipe used for the recycling is suitably arranged somewhat lower (preferably 20 to 40% below the upper drainpipe) than the pipe used for the drainage.

Just as in the case of conventional fermenters, the fluidized-bed fermenter according to the invention can also be provided with the usual auxiliary devices, which make possible tempering, pH control, aeration and/or sterilization of the contents of the fermenter. It can be produced the same way as conventional fermenters made of glass and/or non-corroding metal.

Based on the drawings, the invention is to be explained in more detail.

Figure 2:
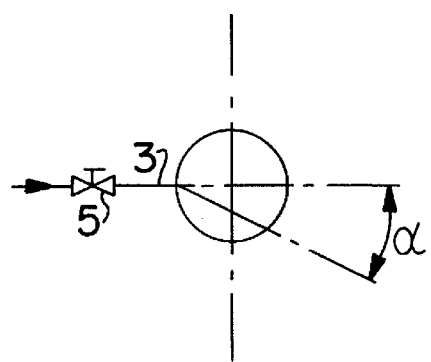
Figure 4:
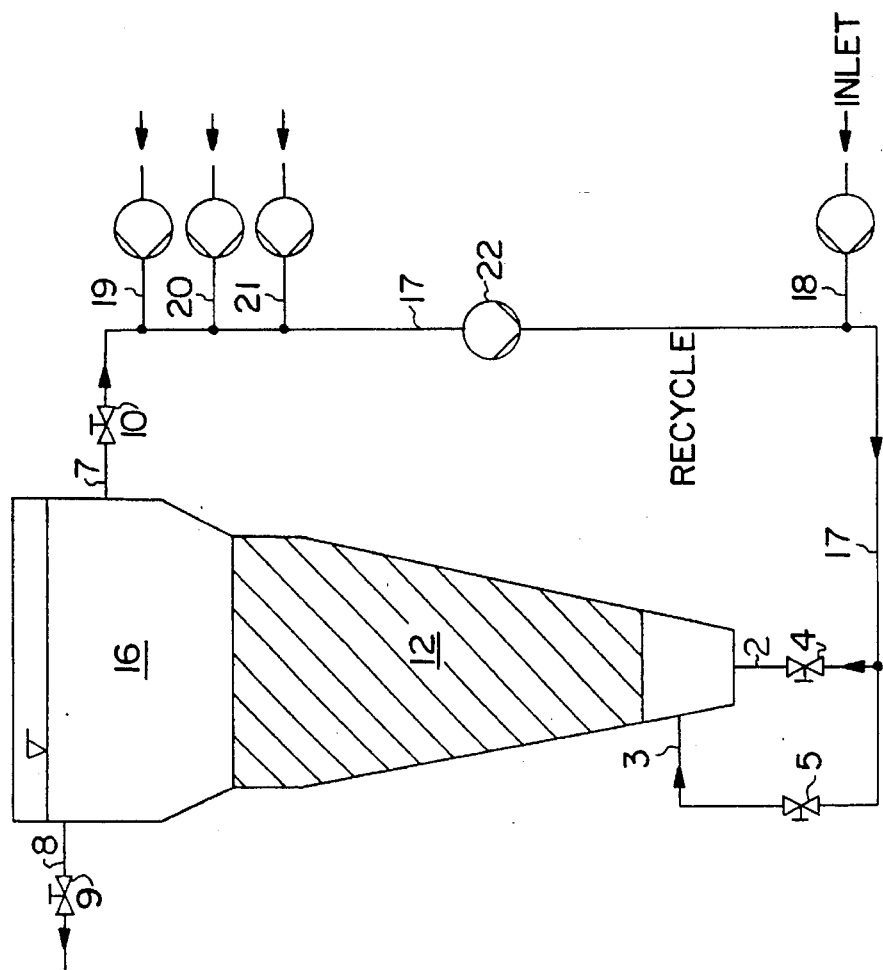
Figure 3:
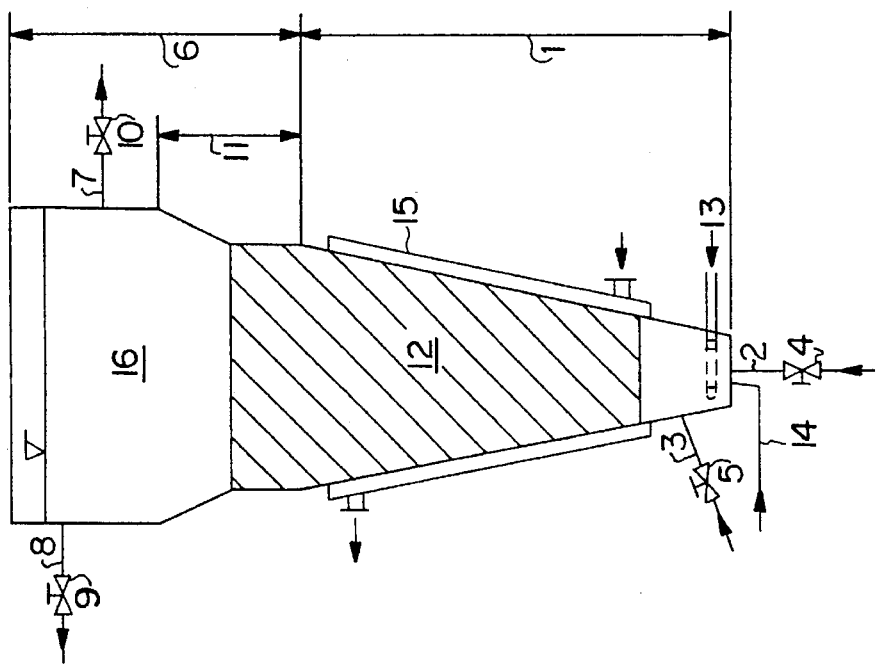
Figure 5:
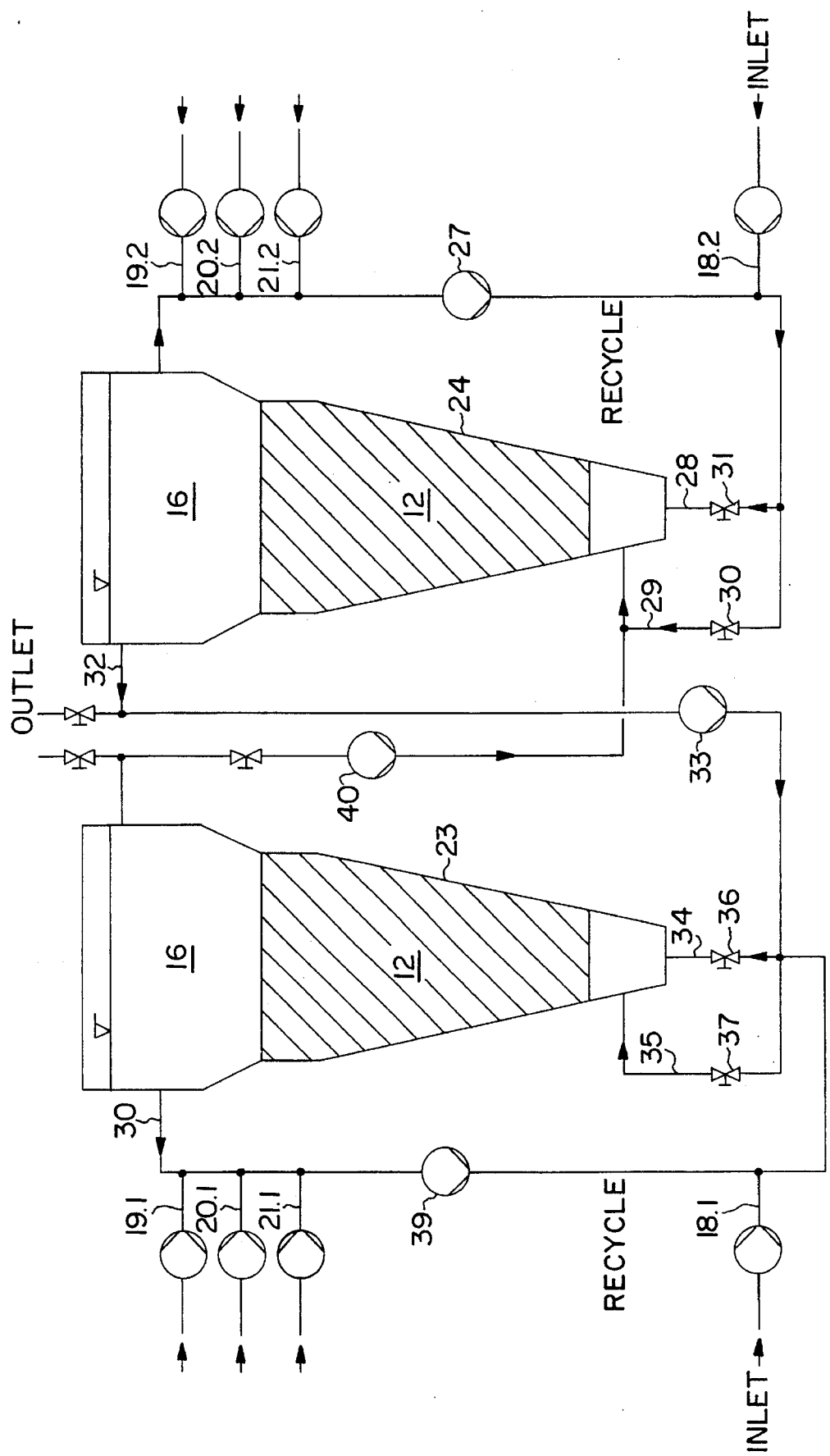

There are shown in:

FIG. 1 a longitudinal section through a fluidized-bed fermenter according to the invention, FIG. 2 a cross section through the fluidized-bed fermenter of FIG. 1 at the level of plane A–B, FIG. 3 a longitudinal section through a fluidized-bed fermenter with built-in tempering, aerating and sterilizing device, FIG. 4 a diagrammatic representation of a fermentation unit with a fluidized-bed fermenter according to the invention and FIG. 5 a diagrammatic representation of a fermentation unit with two fluidized-bed fermenters connected in series.

The fluidized-bed fermenter represented in FIG. 1 is intended for treatment of waste water with bacteria cultures. It consists of cone-shaped fermentation space (1) with truncated cone frustum, sedimentation space (6) as well as feed pipes (2 and 3) provided with control valves (4 and 5) and drainpipes (7 and 8) provided with control valves (9 and 10). Fermentation space (1) has a height of 2300 mm and an upper diameter of 600 mm. Vertical pipe (2) feeds into it and nonhorizontal pipe (3), which is sloped vertically upward and forms an angle of 35° with the horizontal line, at a height of 230 mm. Sedimentation space. (6) is arranged on the upper edge of fermentation space (1). This sedimentation space consists of two cylindrical components provided with a conical enlargement, is closed on top and has an upper diameter of 1300 mm and a total height of 1300 mm. (Hatched area 12 of FIG. 1 is to symbolize the area in which the bacteria culture is whirled. The space identified with number 16 is to symbolize the largely bacteria-free space.) Below the upper cover, two drainpipes (7 and 8) are attached facing one another, of which one pipe (8), used to discharge the fermentation broth, is arranged 250 mm below the upper cover of the sedimentation space, and pipe (9) used as the return is arranged 600 mm below. The fermenter is produced from stainless steel. It can be seen from FIG. 2 that nonvertical feed pipe (3) with the straight line pointing from its intake opening to the fermentation axis forms an angle α of 35°.

The fluidized-bed fermenter represented in FIG. 3 has the same design as that described in FIG. 1, but it has in addition a circular incoming air pipe (13), provided with nozzles, present tight on the bottom; a superheated steam pipe (14), which can be used to sterilize the contents of the fermenter; and a double shell (15) enclosing the fermentation space to accommodate the tempering liquid.

The fermentation unit diagrammatically represented in FIG. 4 basically consists of a fluidized-bed fermenter, as explained in FIG. 1, and a return pipe (17) provided with a metering pump (22) as well as a feed pipe for feeding additives (19) controlling the pH, a feed pipe for feeding $H_2O_2$ as oxygen donor (20), a feed pipe for feeding nutrient medium (21) and a feed pipe for feeding waste water (18), return pipe which is connected by a branching with feed pipes (2 and 3).

1 $m^3$ of waste water and the reflux, concentrated with nutrient medium and adjusted to pH=7, are fed hourly by feed pipe (18) to the fermenter inoculated with a bacteria-mixed culture isolated from the corresponding waste-water sludge, and control valves (4 and 5) of feed pipes (2 and 3) are adjusted so that a stable fluidized bed with constant microorganism density results in the fermenter after the conclusion of the growth phase (about 2 to 6 weeks). Then, 1 $m^3$ of purified waste water is removed hourly from the fermenter by one drainpipe (7) while 7 to 14 $m^3$ of purified waste water is returned to the cycle per hour by other drainpipe (8) to dilute the fed waste water or ground water.

With this fermentation unit, it is possible to purify, continuously per hour, 1 $m^3$ of waste water, which is contaminated with tetrahydrofuran, diethyl ether and diisopropyl ether, over several months, so that it contained at most 5% of the above-mentioned contaminants.

Finally, the fermentation unit diagrammatically represented in FIG. 5 can be mentioned, which is distinguished basically from the device sketched in FIG. 4 in that it has two fermentation units (23 and 24), which in principle have the same design as the unit represented in FIG. 4, in which drainpipe 32 discharging from unit 24 is used to feed waste water or ground water to fermentation unit 23. This unit can be adjusted by corresponding adjustment of the control valves, so that the fermenters are connected in parallel or in series.

It is obvious to one skilled in the art that the fluidized-bed fermenters according to the invention can be used not only for waste-water or ground-water treatment. Possible applications of these fermenters follow, for example, also in the continuous fermentative production of water-soluble alcohols, acids or carbohydrates, such as, for example, ethanol, acetic acid, citric acid, galactose, L-sorbose, the microbial synthesis of amino acids, such as glutamic acid, the production of antibiotics, or the microbiological transformation of steroids.

We claim:

1. A two-phase fluidized-bed fermenter comprising: an inverted substantially frustoconical fermentation space (1) defined by a frustoconical shell formed about an axis, with two feed pipes (2 and 3) for a feeding solution to be fermented connected thereto of which one feed pipe (2) is vertically aligned with the axis and the second pipe (3) is nonvertically aligned with the shell of the cone at a height which is 0.02 to 0.3 times the height of the fermentation space, and a sedimentation space (6) above the fermentation space (1), the sedimentation space having at least one drainpipe (7 or 8).

2. The fluidized-bed fermenter according to claim 1, wherein the upper diameter of fermentation space (1) is 0.1 to 0.8 times the height of the fermentation space.

3. The fluidized-bed fermenter according to claim 1, wherein the fermentation space (1) includes a cylindrical portion at the top thereof.

4. The fluidized-bed fermenter according to claim 1, wherein the vertically-aligned feed pipe (2) and nonvertically-aligned feed pipe (3) are arranged with the nonvertically aligned feed pipe being oblique to the axis wherein a fluidized bed is produced in the fermentation space.

5. The fluidized-bed fermenter according to claim 1, wherein the angle between the longitudinal axis of the nonvertically-aligned feed pipe (3) and the longitudinal axis of the vertical feed pipe (2) does not exceed about 70° with respect to the vertical and 60° with respect to the horizontal.

6. The fluidized-bed fermenter according to claim 1, wherein the sedimentation space (6) comprises at least two cylindrical components joined with a conical enlargement.

7. The fluidized-bed fermenter according to claim 6, wherein the sedimentation space (6) has an upper diameter about 1 to 3 times the upper diameter of the fermentation space (1).

8. The fluidized-bed fermenter according to claim 6, wherein the sedimentation space (6) has a height 0.2 to 0.5 times the height of the fermentation space (1).

9. The fluidized-bed fermenter of claim 1, wherein the fermenter is a two-phase system for treating waste water or ground water without the introduction of air.

10. The fluidized-bed fermenter of claim 9 further including at least one line (19, 20 or 21) connected to the feed pipes (2 and 3) for introducing additional materials into the solution being treated.

11. The fluidized-bed fermenter of claim 10, wherein there are a plurality of lines (19, 20 and 12) connected to a return line (17), the plurality of lines including a feed line (19) for additives for controlling pH, a feed line (20) for feeding $H_2O_2$ and a feed line (21) for feeding nutrient medium.

* * * * *